(12) United States Patent
Kontsos et al.

(10) Patent No.: US 10,488,368 B2
(45) Date of Patent: Nov. 26, 2019

(54) INTEGRATION OF DIGITAL IMAGE CORRELATION WITH ACOUSTIC EMISSION

(71) Applicant: Drexel University, Philadelphia, PA (US)

(72) Inventors: Antonios Kontsos, Philadelphia, PA (US); Ivan Bartoli, Ardmore, PA (US); Prashanth Abraham Vanniamparambil, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 100 days.

(21) Appl. No.: 14/516,708

(22) Filed: Oct. 17, 2014

(65) Prior Publication Data

US 2015/0035950 A1    Feb. 5, 2015

Related U.S. Application Data

(63) Continuation-in-part of application No. PCT/US2013/037252, filed on Apr. 18, 2013.
(Continued)

(51) Int. Cl.
*G01N 29/14*    (2006.01)
*H04N 13/246*    (2018.01)
(Continued)

(52) U.S. Cl.
CPC .......... *G01N 29/14* (2013.01); *G01M 5/0066* (2013.01); *G01M 5/0091* (2013.01);
(Continued)

(58) Field of Classification Search
CPC .......... G01N 29/14; G01N 2291/0232; G01N 2291/0258; G01N 21/8803; G01M 5/0066;
(Continued)

(56) References Cited

U.S. PATENT DOCUMENTS 4,480,480 A * 11/1984 Scott .................. E02B 17/0034
                                                                                    702/41
4,781,455 A    11/1988 Maechler et al.
(Continued)

OTHER PUBLICATIONS

Mao et al. (Multiscale monitoring of interface failure of brittle coating/ductile substrate systems: A non-destructive evaluation method combined digital image correlation with acoustic emission, Journal of Applied Physics, Oct. 18, 2011, vol. 110, No. 8, pp. 084903/1-084903/5.*
(Continued)

*Primary Examiner* — Dave Czekaj
*Assistant Examiner* — Berteau Joisil
(74) *Attorney, Agent, or Firm* — Joseph E. Maenner; Maenner & Associates, LLC

(57) ABSTRACT

An inventive approach is disclosed to integrate Digital Image Correlation (DIC) with the Acoustic Emission method that may be used for structural health monitoring and assessment of critical structural components in civil, mechanical, and aerospace industries. The inventive approach relies on passively recording acoustic emission across the specimen being tested and activating the DIC cameras automatically to measure deformation on the specimen's surface. The resulting acousto-optic system can be used to determine damage initiation, progressive damage development, identify critical regions and make lifetime predictions of the tested specimen.

20 Claims, 8 Drawing Sheets

Related U.S. Application Data

(60) Provisional application No. 61/635,282, filed on Apr. 18, 2012.

(51) Int. Cl.
*G01M 5/00* (2006.01)
*G01N 21/88* (2006.01)
*G06T 7/00* (2017.01)

(52) U.S. Cl.
CPC ....... *G01N 21/8803* (2013.01); *G06T 7/0008* (2013.01); *H04N 13/246* (2018.05); *G01N 2291/0232* (2013.01); *G01N 2291/0258* (2013.01); *G06T 2207/10012* (2013.01); *G06T 2207/30108* (2013.01)

(58) Field of Classification Search
CPC .............. H04N 13/0246; G06T 7/0008; G06T 2207/10012; G06T 2207/301
See application file for complete search history.

(56) References Cited

U.S. PATENT DOCUMENTS

| | | |
|---|---|---|
| 5,757,473 A | 5/1998 | Kanduth et al. |
| 7,377,181 B2 | 5/2008 | Christ, Jr. et al. |
| 2005/0207487 A1* | 9/2005 | Monroe ........... G08B 13/19628 375/240.01 |
| 2007/0209447 A1 | 9/2007 | Christ, Jr. et al. |
| 2008/0105055 A1* | 5/2008 | Ringermacher ....... G01N 23/04 73/643 |
| 2009/0015274 A1* | 1/2009 | Zaykova-Feldman ...................... G01M 7/08 324/750.23 |

OTHER PUBLICATIONS

Mao, W.G. et al., "Multiscale monitoring of interface failure of brittle coating/ductile substrate systems: A non-destructive evaluation method combined digital image correlation with acoustic emission", Journal of Applied Physics, vol. 10, Issue 8. 20011. 8 pages.

International Preliminary Report on Patentability, PCT/US2013/037252, dated Oct. 21, 2014. 9 pages.

International Search Report and Written Opinion, PCT/US2012/037252, dated Jul. 23, 2013. 3 pages.

* cited by examiner

INTEGRATION OF DIGITAL IMAGE CORRELATION WITH ACOUSTIC EMISSION

CROSS-REFERENCE TO RELATED APPLICATION

The present application claims priority from PCT application PCT/US2013/37252, filed on Apr. 18, 2013, which claims priority from U.S. Provisional Patent Application Ser. No. 61/635,282, which was filed on Apr. 18, 2012, and which are incorporated herein in their entireties.

STATEMENT OF GOVERNMENT INTEREST

This invention was made with government support under Contract No. N00014-13-1-0143 awarded by the Office of Naval Research. The government has certain rights in the invention.

BACKGROUND OF THE INVENTION

Field of the Invention

The present invention relates to a nondestructive testing and evaluation (NDT & E) system.

Description of the Related Art

Structural Health Monitoring (SHM) is vital in ensuring the structural integrity of critical components utilized in the aerospace, civil and mechanical industries. The development of SHM has a direct impact on public safety, primarily because it is beneficial in identifying early signs of critical failure and is related to reduced downtime and life extension of aging components and structures.

NDT & E systems are often a crucial part of SHM applications. Currently, no single monitoring technique has been capable of performing complete structural evaluation due to several inherent challenges including unpredictable environmental and loading conditions, limitations of the techniques themselves, lack of an adequately dense sensing network, etc.

Structural integrity monitoring systems based on the Digital Image Correlation (DIC) or the Acoustic Emission (AE) methods currently exist, however they are typically implemented independently and they are operated manually when used to assess material and structural integrity.

Consequently, it would be beneficial to provide an integrated approach in which multiple NDT & E techniques are used to develop an effective SHM system.

BRIEF SUMMARY OF THE INVENTION

Briefly, the present invention provides a NDT & E method of determining the structural integrity of a specimen or structure as external load (e.g. mechanical, thermal, environmental, etc.) is applied. The method comprises the steps of: attaching at least one acoustic sensor to the specimen; applying a contrasting pattern on the surface of the specimen; calibrating a pair of stereoscopic cameras at the contrasting pattern; passively recording acoustic stress waves propagating in the specimen using an AE system electronically coupled to the at least one acoustic sensor; automatically triggering operation of the cameras by the AE system; measuring deformation in the specimen based on load-induced movement of the contrasting pattern in a DIC system, the DIC system being electronically coupled to the cameras; and correlating acoustic stress waves and strain data to determine the structural health of the specimen.

The present invention also provides a digital trigger signal (AE output) that is formed based on real time recorded and naturally occurring acoustic emission information, which is parametrized and used to extract features, based on which the signal is formed and subsequently passed into a DIC system. This trigger signal automatically activates the cameras of a DIC system for adaptive image acquisition depending only upon activity recorded nondestructively by the AE method due to changes in material and or structural integrity.

Additionally, the present invention provides time-synchronization (fusion) of data obtained by the acoustic and optical nondestructive methods for cross-validation and interpretation of information related to material and/or structural integrity.

Further, the present invention provides the control of a mechanical testing machine, in cases when such a machine is used in conjunction with the combined AE and DIC systems, through a digital signal (DIC output) defined in the DIC system based on full field deformation measurements that are further enabled as described above.

BRIEF DESCRIPTION OF THE DRAWINGS

The accompanying drawings, which are incorporated herein and constitute part of this invention, illustrate the presently preferred embodiments of the invention, and, together with the general description given above and the detailed description given below, serve to explain the features of the invention. In the drawings:

FIGS. 5A-C is an exemplary demonstration of triggering the DIC image acquisition by using real time recorded AE information in the partially reinforced concrete masonry wall application shown in FIG. 2C and FIG. 3, wherein FIG. 5A shows the specific AE feature (cumulative energy) as a function of time and correlated with load recorded by a mechanical test machine and also read by the AOSS trends data;

FIG. 5B shows representative images with full field surface strain distribution showing crack initiation;

FIG. 5C shows similar surface strain distribution on the masonry wall that corresponds to the second time instance marked as "Critical Crack Growth" in FIG. 5A;

DETAILED DESCRIPTION OF THE INVENTION

Figure 1:
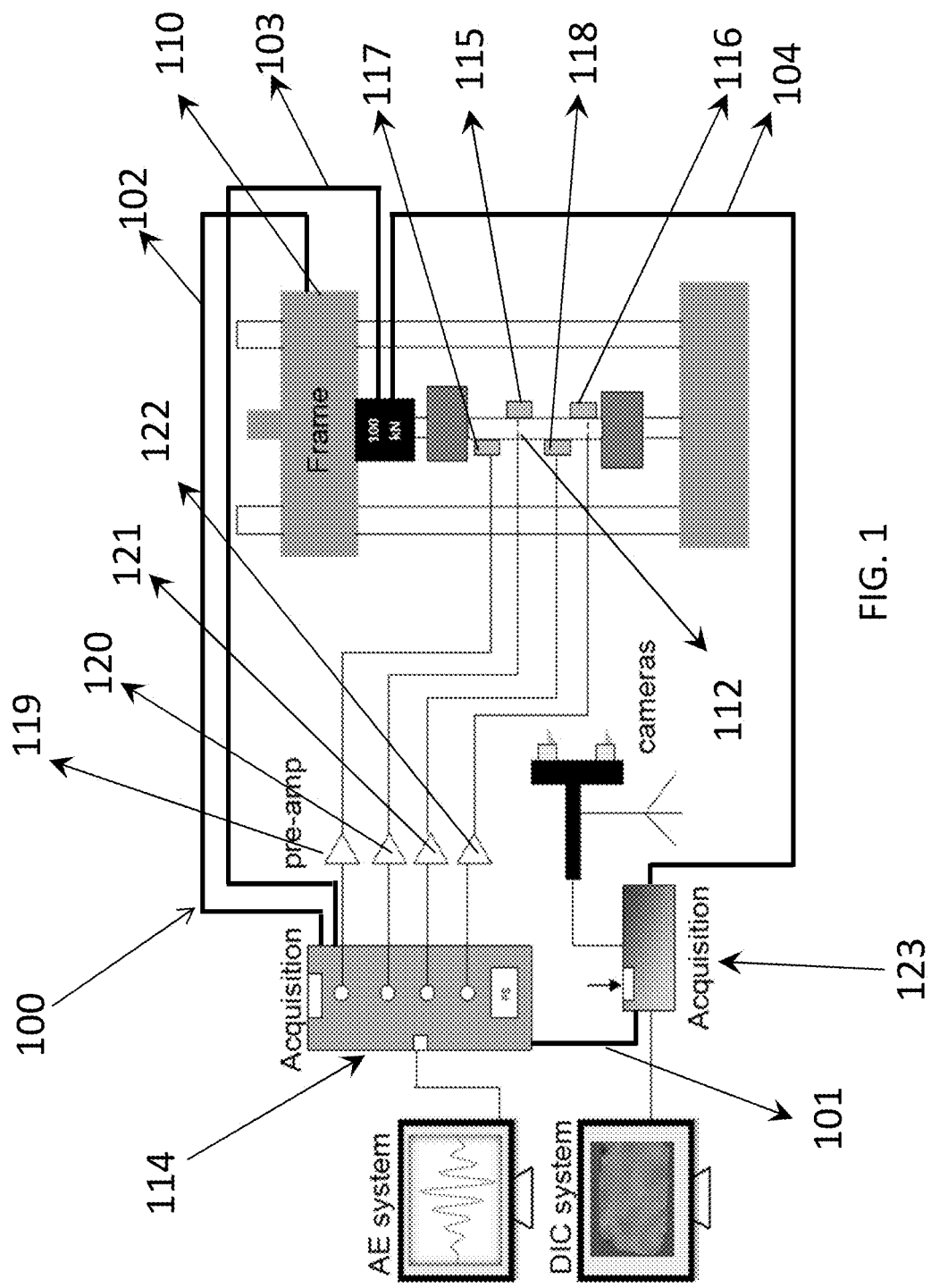
FIG. 1 is a schematic drawing of the Acousto-Optic Sensing System ("AOSS") integrated with a mechanical test machine according to an exemplary embodiment of the present invention.

In the drawings, like numerals indicate like elements throughout. Certain terminology is used herein for convenience only and is not to be taken as a limitation on the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

The present invention includes an optical and an acoustic method to adaptively obtain full field deformation measurements on a material's or structure's surface based on a signal formed by extracting information from volume-related measurements of naturally occurring acoustic emission. This invention, referred to here as "Acousto-Optical Sensing System (AOSS)", describes the communication between its constituents and basis of operation using the Digital Image Correlation (DIC) and Acoustic Emission (AE) methods. The inventive system and method features an approach to activate and trigger recordings in cameras related to DIC based on signals formed and exported by the AE method. This approach can be used to time-synchronize full field deformation measurements with emission of acoustic stress waves occurring in the inspected volume of a material and/or structure by natural causes such as evolving damage due to the application of external loadings, such as, for example, mechanical, thermal, environmental, and other types of loadings.

The present invention also provides a novel approach of integrating in real testing time the DIC with the AE method both at the hardware and at the post processing/analysis levels. The hardware integration between the two techniques is based on user-defined, multi-parametric criteria in the AE system that are used to form a digital output signal. Upon receiving this signal, the DIC cameras are automatically activated and triggered to acquire images based on a user-built script. Consequently, the unique advantage of this hardware integration is an adaptive recording and therefore also memory-storage effective NDE approach that can time-synchronize acoustic with optical information related to material and/or structural failure.

An exemplary AOSS system 100 according to the present invention is shown in FIG. 1. A mechanical test stand 110 is used to apply mechanical load to a test specimen 112, which simulates an object under load. Such object may be a bridge beam, a building column, an airframe, or other structural element that may be under load by its normal operational environment. The load may be a compressive load, a tensile load, a torsional load, a bending load, environmental load, fatigue load or any other load that may be experienced by structural elements. In this particular embodiment, test stand 110 provides axial tensile/compressive loads to a test specimen 112.

Figure 2C:
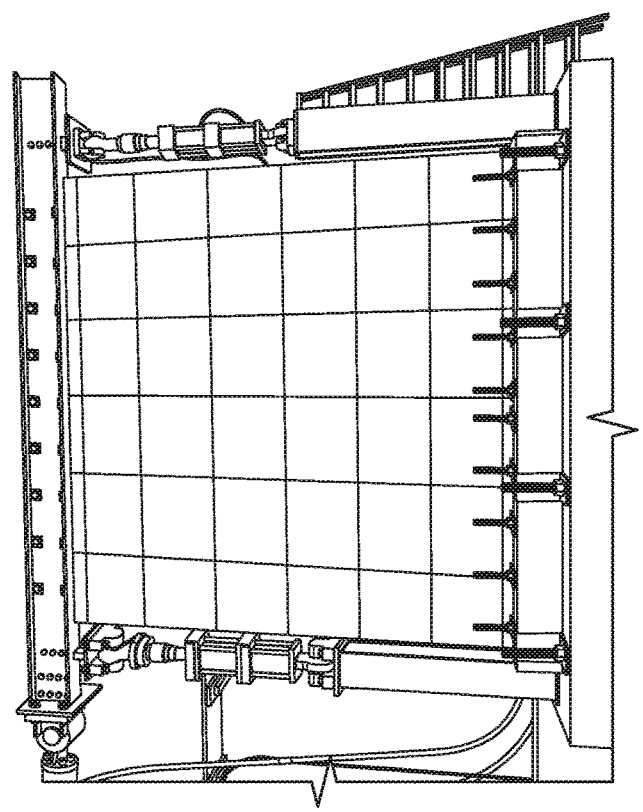
FIG. 2C is an exemplary application of the AOSS for structural testing of a partially reinforced concrete masonry wall subjected to cyclic lateral loading simulating earthquake excitations.
Figure 2B:
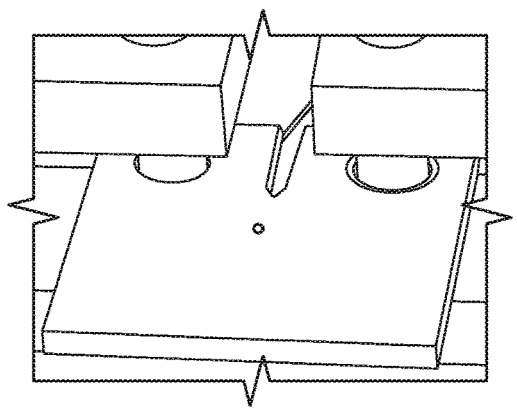
FIG. 2B is an exemplary application of the AOSS for mechanical testing of a laboratory "compact tension" coupon subjected to uniaxial loading that induces cracking.
Figure 2A:
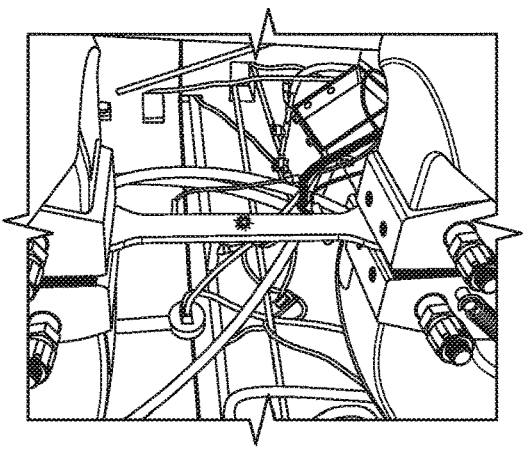
FIG. 2A is an exemplary application of the AOSS for mechanical testing of a laboratory "dog-bone" coupon subjected to uniaxial loading.

Exemplary test specimen 112 is shown in FIG. 2A. Test specimen 112 is an aluminum alloy designed according to (ASTM) standards, although those skilled in the art will recognize that test specimen 112 can be other materials as well. Test specimen 112a in FIG. 2B is another example of the same material with a different specimen geometry based on American Society for Testing and Materials ("ASTM") standards. Test specimen 113 shown in FIG. 2C is a partially reinforced concrete masonry wall to demonstrate the applicability of the AOSS in several materials and at different length scales.

An exemplary AE data acquisition system includes the four-channel DiSP system 114 developed by Physical Acoustics Corporation, schematically shown in FIG. 1. AE system 114 is equipped with four piezoelectric transducers 115-118 and associated preamplifiers 119-122. While a single transducer 115 may be used, additional transducers 116-118 may be used as receivers that passively receive acoustic stress waves propagating through test specimen 112, 113 during testing. Further, while piezoelectric transducers are used, other sensors technologies, such as fiber bragg and MEMS sensors can be used. Such sensing technologies are referred to as "acoustic sensors" in the remainder of this text. The system 114 shown in FIG. 1 has analog inputs that allow load and displacement/strain recordings from the mechanical test stand 110.

Figure 3B:
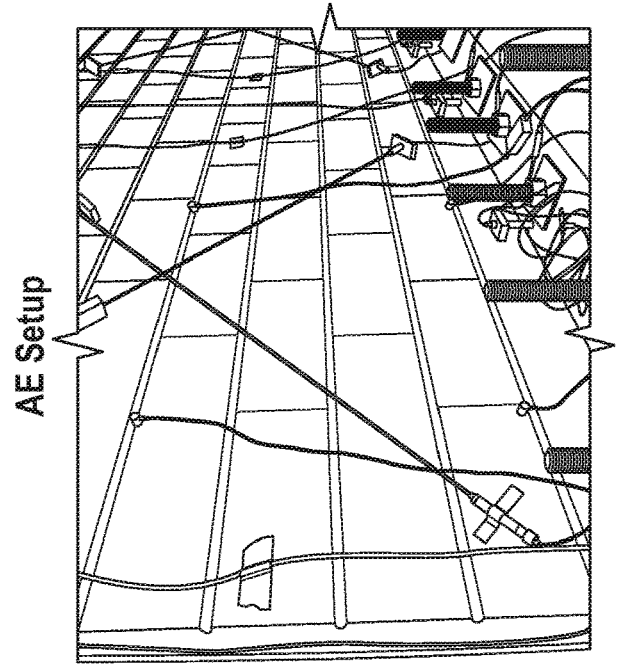
FIG. 3B is an exemplary demonstration of the AE sensor setup in the AOSS for structural testing of the partially reinforced masonry wall shown in FIG. 3A.
Figure 3A:
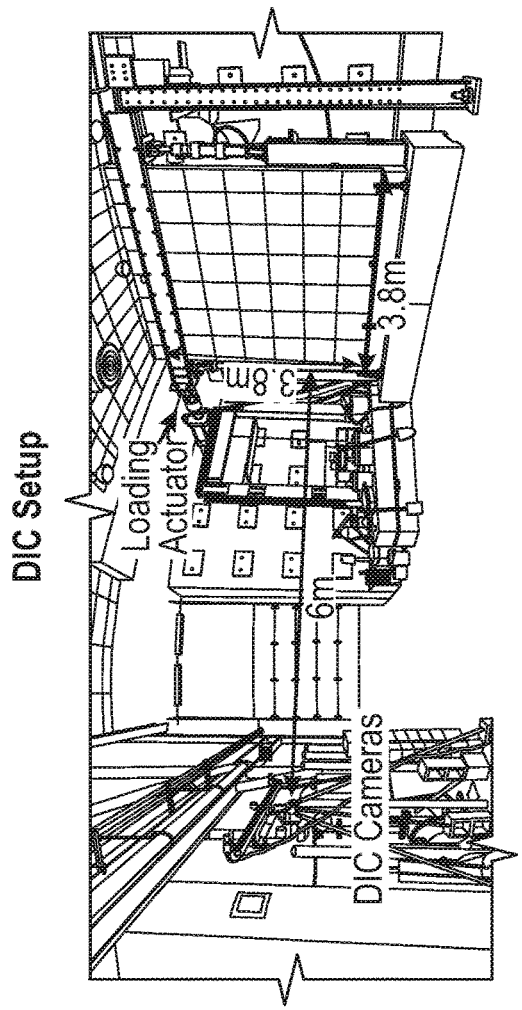
FIG. 3A is an exemplary demonstration of a DIC camera setup in the AOSS for structural testing of a partially reinforced masonry wall subjected to cyclic lateral loading simulating earthquake excitations.

The exemplary DIC data acquisition system 123 is a GOM ARAMIS 3D 5-megapixel camera system with analog inputs that allow load recording from the mechanical test stand 110. In addition, the data acquisition of the DIC system 123 also supports input/output ports that can trigger the cameras to activate and record images based on an external trigger. Exemplary 5-megapixel cameras are Baumer TGX15 124-125, shown in FIG. 3A.

The AE system 114 is electronically connected to the DIC system using BNC cables and an external parametric box, shown at 101 in FIG. 1, so that information in the form of input/output signals between the AE system 114 and the DIC system 123 can be exchanged in real experimental time. An exemplary The direct connection between the AE system 14 and the DIC system 123 enables the DIC system 123 to be automatically activated and triggered to acquire images based on a TTL signal generated by the AE system 114. Additionally, the AE system 114 is connected using BNC cables 102 to test stand 110 and to a load cell 105 using BNC cables 103. Thus, the AE system 114 is also equipped to receive load/displacement or any other parametric input in real time through a parametric box. Further, the DIC system 123 is connected to the load cell 105 by BNC cables 104. A closed loop is formed between test stand 110, DIC system 123, and AE system 114 so that information (for example, load) recorded from one system can be passed to other systems (for example AE and DIC) and synchronized at both the time and loading stages.

For DIC measurements, a contrasting speckle pattern must be present on the surface of test specimens 112-113. In this case, a random speckle pattern is applied on the surface of test specimens 112-113 for tracking deformation, and pretest images of test specimens 112-113 are taken to determine the sensitivity of system 123 for a particular field of view. The random speckle pattern is used to identify the relative displacement of test specimens 112-113 by correlating the acquired images to a known reference image under load.

In an alternative embodiment, such as, for example, determining strain in a bridge beam (not shown), if natural surface contrasts are readily present on the beam, such as, for example, dirt, paint chips, or any other random pattern, then the random speckle pattern does not necessarily need to be applied to the beam. In such a situation, a load is already present in the beam and the piezoelectric transducers 115-118 are attached to the beam after the load has been applied to the beam.

Figures 4A, 4B:
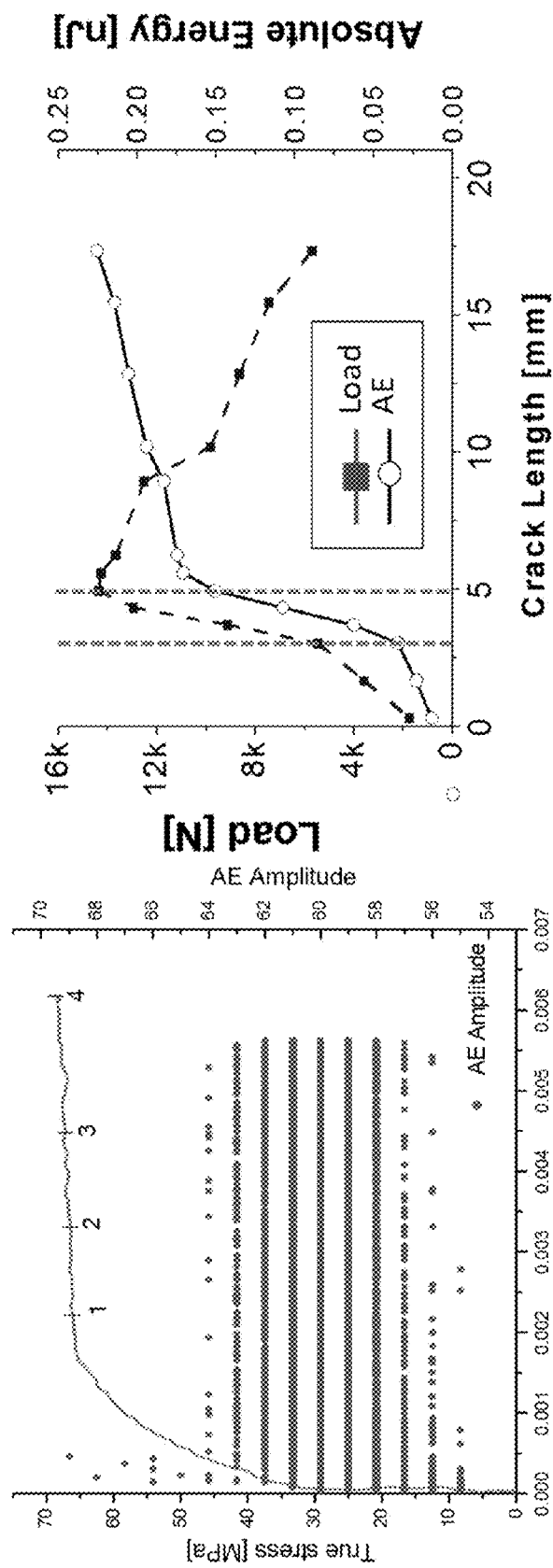
FIG. 4A is a graph overlaying stress values obtained by the AOSS with the average full field vertical strain (true strain) calculated by the DIC system and the AE amplitude distribution extracted by real-time recorded AE waveforms of voltage versus time, with the true stress recorded by the AOSS using real time information from the mechanical testing machine.
FIG. 4B is a graph overlaying load values obtained by a mechanical test machine with the crack length measured by the DIC system and the cumulative absolute energy computed by the recorded AE as loading is applied to a compact tension coupon similar to FIG. 3B.

As an exemplary method, true stress (calculated by using data recorded by the load cell of the test stand) versus true strain (calculated by using the DIC system), while AE data (AE waveform amplitude distribution) has been synchronized and added to the true stress-true strain curve in FIG. 4A. As an additional exemplary method, crack length monitoring (computed by the DIC system) as a function of applied (by the test stand) load and the cumulative absolute energy (computed by the AE system) is shown in FIG. 4B. The AE system and the features extracted or computed by it were used in the examples shown to activate and record data by the DIC system.

Figures 5A, 5B, 5C:
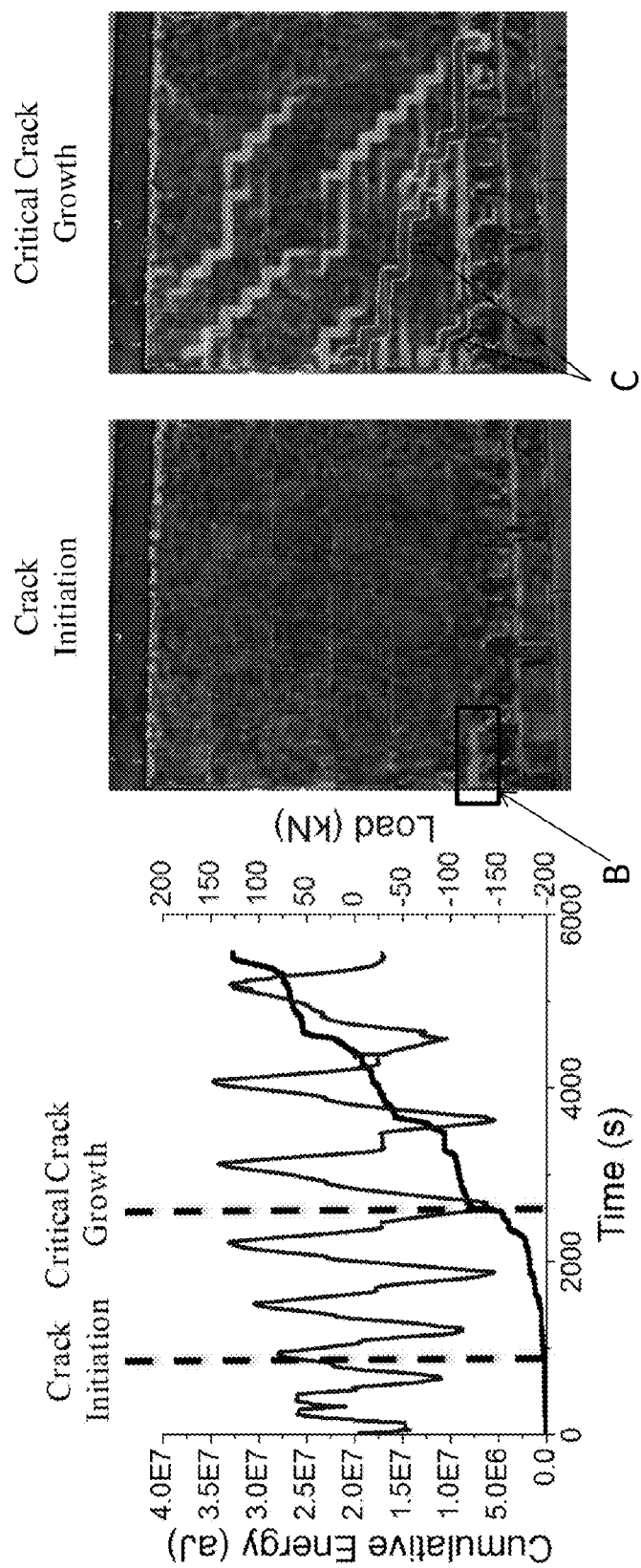

Additional exemplary correlations between DIC, AE and mechanical test data are shown in FIG. 5A in case of cyclic loading of a structural component. The cumulative energy computed by the AE system is synchronized with load information and is used to trigger the cameras of the DIC system that record full field images of surface deformation (in this case strain) as shown in FIG. 5.

FIG. 5A shows the specific AE feature (cumulative energy as a function of time and correlated with load recorded by the mechanical test machine and also read by the AOSS trends data. Note the two time instances denoted by the two vertical broken lines and labeled as "Crack Initiation" and "Critical Crack Growth". Changes in the AE features at this time instances were used to trigger the DIC system and record full field surface strain information as shown in FIGS. 5B and 5C.

FIG. 5B shows representative images with full field surface strain distribution showing crack initiation, noted by the box "B" on the bottom left corner of the Figure, which corresponds to the first time instance marked in FIG. 5A.

FIG. 5C shows similar surface strain distribution on the masonry wall that corresponds to the second time instance marked as "Critical Crack Growth" in FIG. 5A. The lines marked "C" correspond to regions on the wall with more pronounced crack formation and grown in a staircase pattern.

Figure 6A:
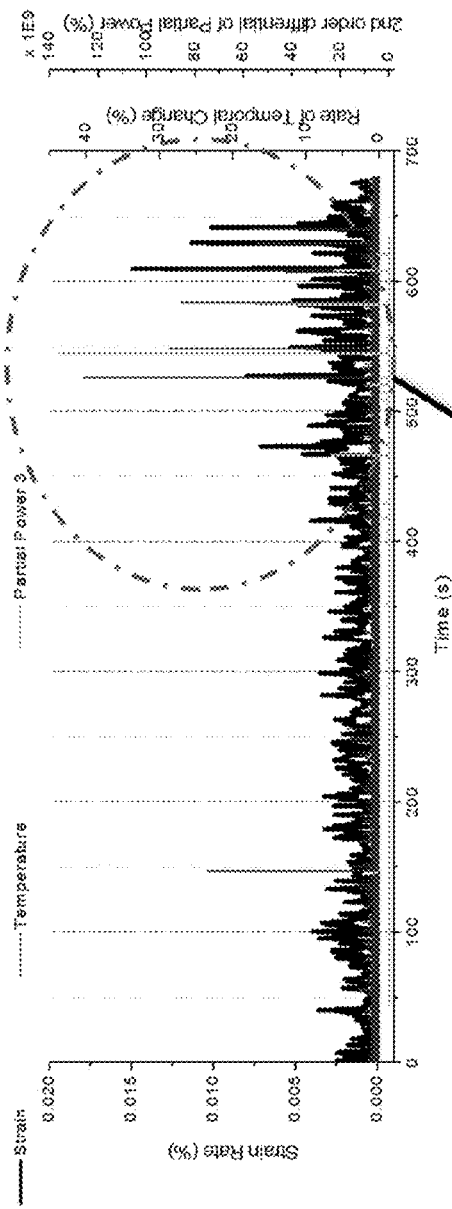
FIG. 6A is a graph demonstrating time-synchronization of information collected by the AOSS by using data obtained by the DIC (strain), AE (Partial Power 3) and an added infrared thermography system (surface temperature) in an exemplary application in the case of the compact tension coupon test shown in FIG. 2B.
Figure 6B:
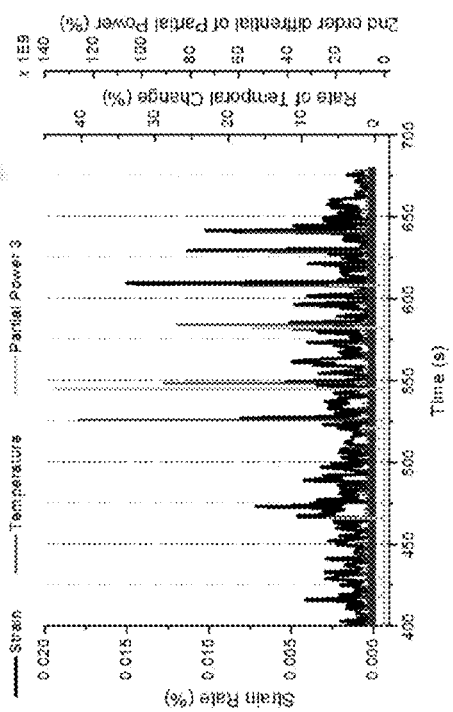
FIG. 6B is an enlargement of a portion of the graph of FIG. 6A marked by the broken line that shows the time synchronization of the three different datasets achieved by the AOSS.

In FIGS. 6A and 6B, the measured strain by the DIC system after receiving feedback from the AE system is plotted against a calculated AE feature (partial power, which is an AE parameter that can be extracted from digital signal processing) as well as the surface temperature change of the specimen measured by an addition to the exemplary AOSS which in this case also comprises an infrared thermography camera (not shown).

Figure 7:
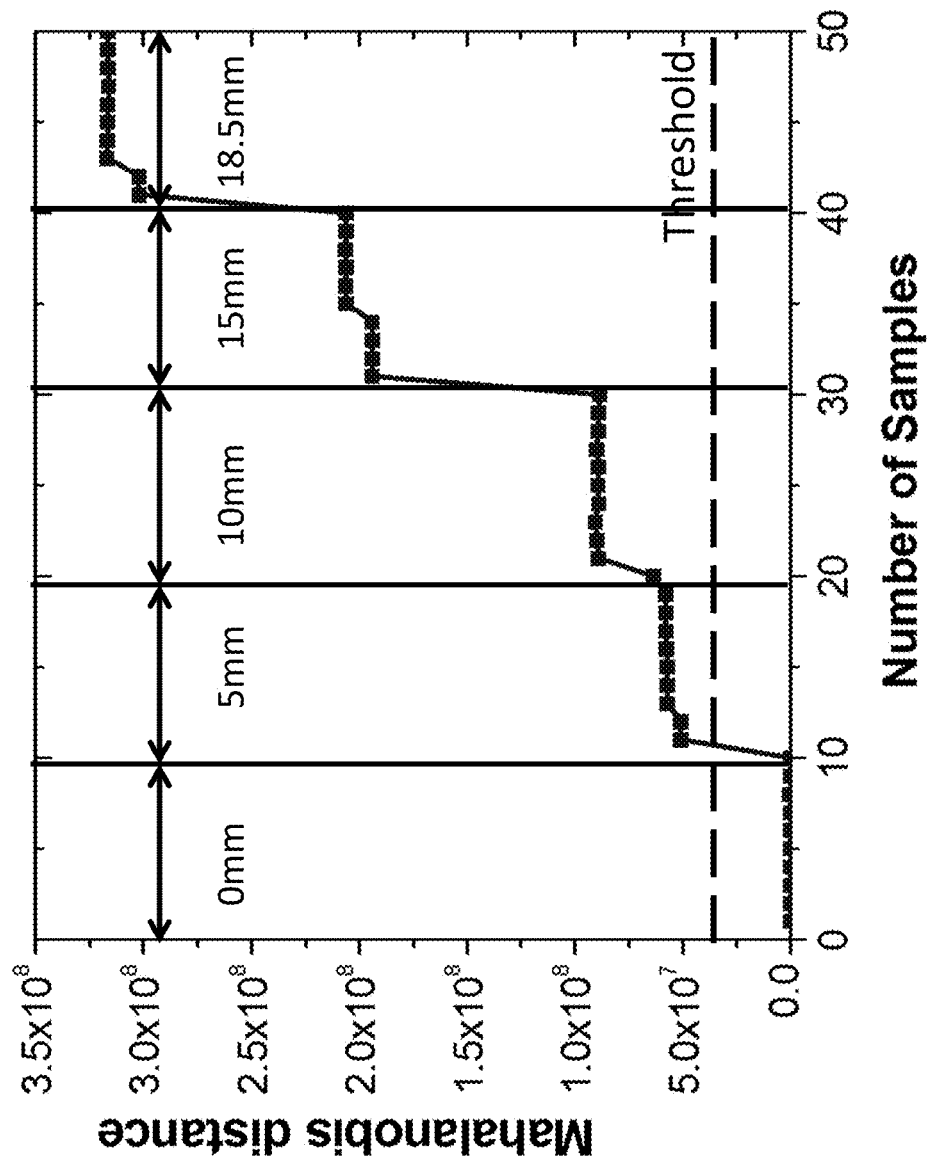
FIG. 7 is an exemplary application of integrating information (data fusion) obtained by the AOSS for damage diagnosis in the case of the compact tension coupon test shown in FIG. 2B, with the Mahalanobis distance being defined as a parameter using information from both DIC and AE in the AOSS.

In FIG. 7, a parameter based on what is known as Mahalanobis distance was calculated by using features recorded by both the AE and DIC system, after the DIC system was triggered by the AE system; this parameter is used to detect the extent of damage (in this case length of crack in an experiment similar to the experiment illustrated in in FIG. 2B).

Figure 8A:
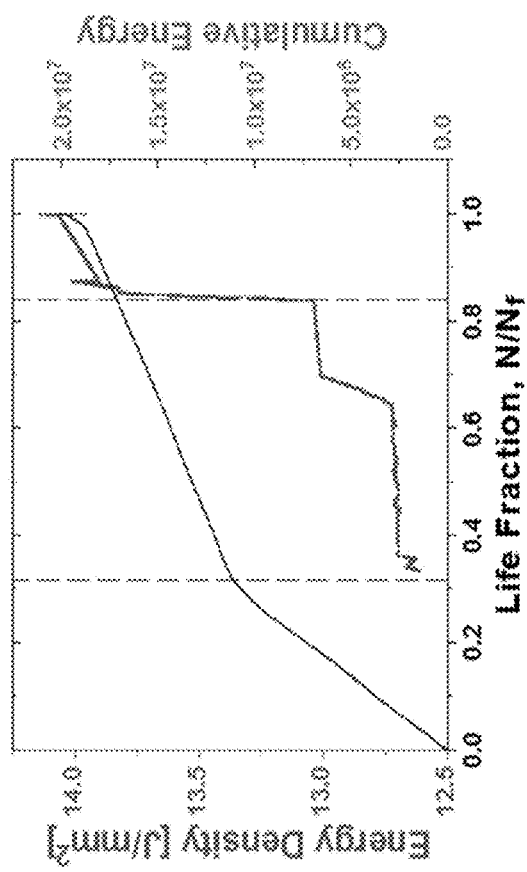
FIG. 8A is a graph highlighting the correlation between DIC (residual stiffness) and AE (cumulative energy) data with lifetime fractions of a laboratory coupon similar to the laboratory coupon shown in FIG. 2A.
Figure 8B:
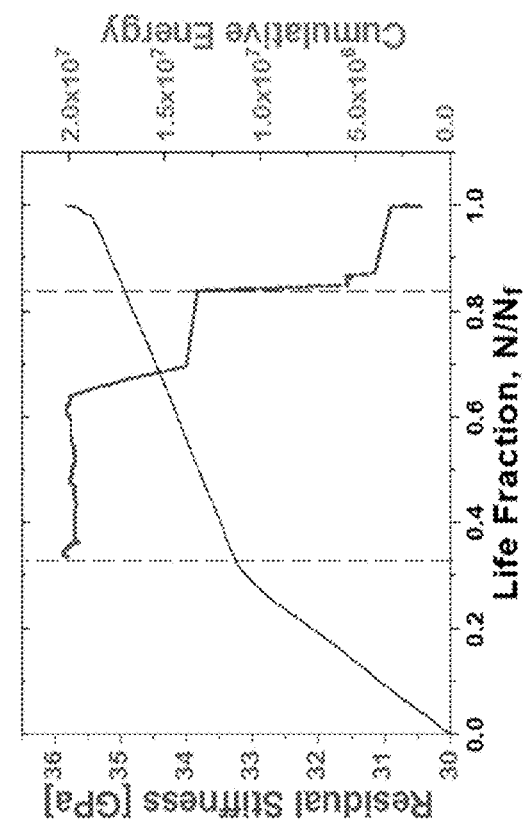
FIG. 8B is another graph highlighting the correlation between DIC (energy density) and AE (cumulative energy) data with lifetime fractions of a laboratory coupon.

In FIG. 8 an exemplary application of how the demonstrated AOSS is used to predict the life fraction of a material or structural component is presented by plotting parameters computed by using DIC data (residual stiffness in FIG. 8A and energy density in FIG. 8B) with the cumulative energy computed based on AE data. Note that DIC data were recorded after triggering of the DIC system using an input signal based on changes of the AE data.

The advantages of the inventive Acoustic-Optical Sensing system include seamless integration of AE with DIC, in that AE and DIC are now capable of communicating with each other without manual intervention. Consequently, this novel setup provides deformation measurements through the DIC system based on criteria defined in the AE system. Further, the novel system provides the capability to acquire DIC imagery only when identified by the operator as "critical" AE information is recorded, thereby enabling digital memory savings in the DIC system. This aspect could be particularly useful in long-term SHM applications.

Additionally, the novel AOSS provides the opportunity to integrate full field mechanical parameters such as in- and out-of-plane deformation measurements and material properties including Poisson's ratio with time, frequency and joint time-frequency AE features such as amplitude, peak frequency, partial powers, and other known parameters. This combination of information enables a cross-validated evaluation of material and/or structural integrity which increases the reliability of the measurements recorded by each of the two systems independently.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A nondestructive method of determining the structural integrity and making life fraction predictions of a -specimen as a load is applied to the specimen, the method comprising the steps of:
    attaching at least one acoustic emission sensor to the specimen;
    applying a contrasting pattern on the surface of the specimen;
    calibrating a pair of stereoscopic cameras at the contrasting pattern;
    passively recording acoustic stress waves propagating in the specimen in an Acoustic Emission (AE) system electronically coupled to the at least one acoustic sensor and generating AE data;
    time synchronizing cumulative energy calculated from the AE data with information about the load:
    triggering operation of the cameras by the AE system based on changes of the AE data;
    adaptively recording data generated by operation of the cameras;
    measuring deformation in the specimen based on load-induced movement of the contrasting pattern in a Digital Image Correlation (DIC) system, the DIC system being electronically coupled to the cameras; and
    correlating stress waves traveling through the specimen and strain data measured on a surface of the specimen to determine the structural health of the specimen and making a life fraction prediction of the specimen.

2. The method according to claim 1, further comprising, after calibrating the cameras at the contrasting pattern, applying a load to the specimen.

3. The method according to claim 2, wherein the load applying step comprises attaching the specimen to a load applying test stand.

4. The method according to claim 3, wherein the at least one acoustic emission sensor and the cameras are electrically connected to the test stand.

5. A nondestructive method of determining the structural integrity and making life fraction predictions of a specimen as a load is applied to the specimen, the method comprising the steps of:
    attaching at least one acoustic emission sensor to the specimen;
    applying a contrasting pattern on the surface of the specimen;
    calibrating a pair of stereoscopic cameras at the contrasting pattern; applying a load to the specimen;
    passively recording acoustic stress waves propagating in the specimen in an Acoustic Emission (AE) system electronically coupled to the at least one acoustic sensor;
    triggering operation of the cameras by the AE system;
    measuring deformation in the specimen based on load-induced movement of the contrasting pattern in a Digital Image Correlation (DIC) system, the DIC system being electronically coupled to the cameras; and
    correlating stress waves travelling through the specimen and strain data measured on a surface of the specimen to determine the structural health of the specimen and making a life fraction prediction of the specimen, wherein a digital output is sent from the AE system to the DIC system.

6. The method according to claim 4, further comprising triggering the DIC cameras based on an input signal received from the AE system.

7. The method according to claim 6, wherein the correlating step comprises measuring deformation in the specimen synchronized with the applied load and acoustic activity.

8. The method according claim 7, wherein the correlating step comprises computing a life fraction of the specimen by using synchronized DIC and AE data.

9. The method according to claim 1, wherein the at least one acoustic sensor comprises a plurality of acoustic sensors.

10. A method of determining the structural integrity and making life fraction predictions of a specimen as a load is applied to the specimen, the method comprising the steps of:
    attaching at least one acoustic emission sensor to the specimen;
    determining a contrasting pattern on the surface of the specimen;
    aiming two cameras at the contrasting pattern;
    passively recording acoustic stress waves propagating in the specimen in an Acoustic Emission (AE) system electronically coupled to the at least one acoustic sensor;
    triggering operation of the cameras by the AE system;
    determining strain in the specimen and making a life fraction prediction of the specimen based on load-induced movement of the contrasting pattern; and
    correlating stress waves travelling through the specimen and strain data measured on a surface of the specimen to determine the structural health of the specimen and making a life fraction prediction of the specimen.

11. The method according to claim 10, wherein the step of determining the contrast pattern comprises applying a speckle pattern.

12. The method according to claim 10, further comprising, after aiming the two cameras at the contrasting pattern, applying a load to the specimen.

13. The method according to claim 12, wherein the load applying step comprises attaching the specimen to a load applying test stand.

14. The method according to claim 13, wherein the at least one acoustic emission sensor and the two cameras are electrically connected to the test stand.

15. The method according to claim 14, wherein the test stand varies the applied load based on electronic information transmitted to the test stand during the strain measurement step.

16. The method according to claim 10, wherein the acoustic emission sensor attaching step comprises attaching the at least one acoustic sensor to the specimen before the load has been applied to the specimen.

17. The method according to claim 16, wherein the correlating step comprises measuring strain in the specimen as a function of applied load and acoustic emission activity.

18. The method according claim 10, wherein the correlating step comprises measuring a life fraction of the specimen versus the energy density value.

19. The method according to claim 10, wherein the correlating step further comprises measuring the life fraction of the specimen versus cumulative acoustic emission energy.

20. The method according to claim 10, wherein the correlating step comprises measuring a life fraction of the specimen versus the residual stiffness of the specimen.

* * * * *